United States Patent
Orlandin et al.

(10) Patent No.: US 11,566,058 B2
(45) Date of Patent: Jan. 31, 2023

(54) PROCESS FOR THE PREPARATION OF HIGH PURITY GLUCAGON

(71) Applicant: FRESENIUS KABI IPSUM S.R.L., Cassina de' Pecchi (IT)

(72) Inventors: Andrea Orlandin, Cassina de' Pecchi (IT); Antonio Ricci, Cassina de' Pecchi (IT); Walter Cabri, Cassina de' Pecchi (IT); Steve McIntyre, Craigavon (GB); Alex Saunders, Belfast (GB)

(73) Assignee: Fresenius Kabi iPSUM S.R.L., Milan (IT)

( * ) Notice: Subject to any disclaimer, the term of this patent is extended or adjusted under 35 U.S.C. 154(b) by 0 days.

(21) Appl. No.: 16/905,474

(22) Filed: Jun. 18, 2020

(65) Prior Publication Data

US 2020/0399339 A1    Dec. 24, 2020

(30) Foreign Application Priority Data

Jun. 18, 2019 (EP) .................................... 19180871

(51) Int. Cl.
  *C07K 14/605* (2006.01)
  *C07K 1/06* (2006.01)
(52) U.S. Cl.
  CPC ............ *C07K 14/605* (2013.01); *C07K 1/063* (2013.01)
(58) Field of Classification Search
  CPC .... C07K 14/605; C07K 1/063; C07K 14/001; A61K 38/00
  See application file for complete search history.

(56) References Cited

U.S. PATENT DOCUMENTS

| | | | |
|---|---|---|---|
| 3,642,763 A | 2/1972 | Wunsch et al. | |
| 4,826,763 A | 5/1989 | Norris et al. | |
| 6,110,703 A | 8/2000 | Egel-Mitani et al. | |
| 10,414,829 B2 | 9/2019 | Cabri et al. | |
| 10,414,830 B2 | 9/2019 | Cabri et al. | |
| 10,544,109 B2 | 1/2020 | Singh et al. | |
| 10,577,433 B2 | 3/2020 | Cabri et al. | |
| 10,800,763 B2 | 10/2020 | Cabri et al. | |
| 2018/0244635 A1 | 8/2018 | Singh et al. | |
| 2018/0312494 A1 | 11/2018 | Cabri et al. | |
| 2018/0346608 A1 | 12/2018 | Cabri et al. | |
| 2018/0355070 A1 | 12/2018 | Cabri et al. | |
| 2019/0100569 A1* | 4/2019 | Loidl | C07K 1/061 |
| 2019/0218249 A1 | 7/2019 | Cabri et al. | |
| 2019/0241511 A1 | 8/2019 | Male et al. | |
| 2019/0284308 A1 | 9/2019 | Cabri et al. | |
| 2020/0031850 A1 | 1/2020 | Pandey et al. | |
| 2020/0140427 A1 | 5/2020 | Tomar et al. | |
| 2020/0181133 A1 | 6/2020 | Cabri et al. | |
| 2020/0277295 A1 | 9/2020 | Sokhi et al. | |
| 2020/0399339 A1 | 12/2020 | Orlandin et al. | |

FOREIGN PATENT DOCUMENTS

| | | |
|---|---|---|
| CN | 103333239 A | 10/2013 |
| WO | WO 2007/147816 A1 | 12/2007 |
| WO | WO 2010/070255 A1 | 6/2010 |
| WO | WO 2017/162650 A1 | 9/2017 |
| WO | WO 2020/254479 A1 | 12/2020 |

OTHER PUBLICATIONS

U.S. Appl. No. 15/735,855, filed Dec. 12, 2017.
U.S. Appl. No. 15/757,259, filed Mar. 2, 2018.
U.S. Appl. No. 15/779,038, filed May 24, 2018.
U.S. Appl. No. 15/779,040, filed May 24, 2018.
U.S. Appl. No. 16/087,065, filed Sep. 20, 2018.
U.S. Appl. No. 16/317,492, filed Jan. 11, 2019.
U.S. Appl. No. 16/332,717, filed Mar. 12, 2019.
U.S. Appl. No. 16/484,346, filed Aug. 7, 2019.
U.S. Appl. No. 16/627,160, filed Dec. 27, 2019.
U.S. Appl. No. 16/705,275, filed Dec. 6, 2019.
U.S. Appl. No. 16/758,773, filed Apr. 23, 2020.
U.S. Appl. No. 17/048,988, filed Oct. 19, 2020.
U.S. Appl. No. 17/061,111, filed Oct. 1, 2020.
Cardona et al., "Application of Dmb-Dipeptides in the Fmoc SPPS of Difficult and Aspartimide-Prone Sequences," *Int J Pept Res Ther* 14: 285-292 (2008).
Haack et al., "Serine Derived Oxazolidines as Secondary Structure Disrupting, Solubilizing Building Blocks in Peptide Synthesis," *Tetrahedron Letters* 33(12):1589-1592 (1992).
Mergler et al., "Bachem—Insights into Peptide Chemistry Achievements by the World's Leading Independent Manufacturer of Peptides," *Chimia International Journal for Chemistry* 67(12): 874-880 (2013).
Sampson et al., "The Synthesis of 'Difficult' Peptides Using 2-Hydroxy-4-Methoxybenzyl or Pseudoproline Amino Acid Building Blocks: a Comparative Study," *J Peptide Sci* 5(9): 403-409 (1999).
Zahariev et al., "Synthesis of 'difficult' peptides free of aspartimide and related products, using peptoid methodology," *Tetrahedron Letters* 47: 4121-4124 (2006).
European Patent Office, Extended European Search Report in European Patent Application No. 19180871.6 (dated Nov. 25, 2019).

* cited by examiner

*Primary Examiner* — Sudhakar Katakam
(74) *Attorney, Agent, or Firm* — Leydig, Voit & Mayer, Ltd.

(57) ABSTRACT

The present invention provides an improved process for the preparation of high purity glucagon comprising the use of Xmb-protected amino acids, wherein may Xmb include, e.g., 2,4,6-trimethoxybenzyl, 2,4-dimethoxybenzyl, or 2-hydroxy-4-methoxybenzyl. The process also comprises the use of building blocks such as pseudoprolines to avoid aggregation and obtain the product in high yield and purity.

10 Claims, No Drawings

Specification includes a Sequence Listing.

SEQUENCE LISTING

<160> NUMBER OF SEQ ID NOS: 21

<210> SEQ ID NO 1
<211> LENGTH: 29
<212> TYPE: PRT
<213> ORGANISM: human
<220> FEATURE:
<221> NAME/KEY: glucagon
<222> LOCATION: (1)..(29)

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 26
<212> TYPE: PRT
<213> ORGANISM: artificial
<220> FEATURE:
<223> OTHER INFORMATION: C-terminal peptide with Xmb-Gly and
      pseudoproline pDS
<220> FEATURE:
<221> NAME/KEY: Xaa
<222> LOCATION: (1)..(1)
<223> OTHER INFORMATION: Xmb-protected glycine
<220> FEATURE:
<221> NAME/KEY: MISC_FEATURE
<222> LOCATION: (2)..(2)
<223> OTHER INFORMATION: optionally contains a side chain protecting
      group
<220> FEATURE:
<221> NAME/KEY: MISC_FEATURE
<222> LOCATION: (4)..(10)
<223> OTHER INFORMATION: each amino acid optionally contains a side
      chain protecting group
<220> FEATURE:
<221> NAME/KEY: Xaa
<222> LOCATION: (12)..(13)
<223> OTHER INFORMATION: Asp-Ser pseudoproline protected dipeptide
<220> FEATURE:
<221> NAME/KEY: MISC_FEATURE
<222> LOCATION: (14)..(15)
<223> OTHER INFORMATION: each amino acid optionally contains a side
      chain protecting group
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (21)..(22)
<223> OTHER INFORMATION: each amino acid optionally contains a side
      chain protecting group
<220> FEATURE:
<221> NAME/KEY: MISC_FEATURE
<222> LOCATION: (25)..(26)
<223> OTHER INFORMATION: each amino acid optionally contains a side
      chain protecting group

<400> SEQUENCE: 2

Xaa Thr Phe Thr Ser Asp Tyr Ser Lys Tyr Leu Xaa Xaa Arg Arg Ala
1               5                   10                  15

Gln Asp Phe Val Gln Trp Leu Met Asn Thr
            20                  25

<210> SEQ ID NO 3
<211> LENGTH: 26
<212> TYPE: PRT
<213> ORGANISM: Artificial Sequence
<220> FEATURE:
<223> OTHER INFORMATION: C-terminal peptide with Xmb-Gly and
      pseudoproline pYS
<220> FEATURE:
<221> NAME/KEY: Xaa
<222> LOCATION: (1)..(1)
<223> OTHER INFORMATION: Xmb-protected glycine
<220> FEATURE:
<221> NAME/KEY: MISC_FEATURE
<222> LOCATION: (2)..(2)
<223> OTHER INFORMATION: optionally contains a side chain protecting
      group
<220> FEATURE:
<221> NAME/KEY: MISC_FEATURE
<222> LOCATION: (4)..(6)

```
<223> OTHER INFORMATION: each amino acid optionally contains a side
      chain protecting group
<220> FEATURE:
<221> NAME/KEY: Xaa
<222> LOCATION: (7)..(8)
<223> OTHER INFORMATION: Tyr-Ser pseudoproline protected dipeptide
<220> FEATURE:
<221> NAME/KEY: MISC_FEATURE
<222> LOCATION: (9)..(10)
<223> OTHER INFORMATION: each amino acid optionally contains a side
      chain protecting group
<220> FEATURE:
<221> NAME/KEY: MISC_FEATURE
<222> LOCATION: (12)..(15)
<223> OTHER INFORMATION: each amino acid optionally contains a side
      chain protecting group
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (21)..(22)
<223> OTHER INFORMATION: each amino acid optionally contains a side
      chain protecting group
<220> FEATURE:
<221> NAME/KEY: MISC_FEATURE
<222> LOCATION: (25)..(26)
<223> OTHER INFORMATION: each amino acid optionally contains a side
      chain protecting group

<400> SEQUENCE: 3

Xaa Thr Phe Thr Ser Asp Xaa Xaa Lys Tyr Leu Asp Ser Arg Arg Ala
1               5                   10                  15

Gln Asp Phe Val Gln Trp Leu Met Asn Thr
            20                  25

<210> SEQ ID NO 4
<211> LENGTH: 26
<212> TYPE: PRT
<213> ORGANISM: Artificial Sequence
<220> FEATURE:
<223> OTHER INFORMATION: C-terminal peptide with Xmb-Gly and
      pseudoproline pTS
<220> FEATURE:
<221> NAME/KEY: Xaa
<222> LOCATION: (1)..(1)
<223> OTHER INFORMATION: Xmb-protected glycine
<220> FEATURE:
<221> NAME/KEY: MISC_FEATURE
<222> LOCATION: (2)..(2)
<223> OTHER INFORMATION: optionally contains a side chain protecting
      group
<220> FEATURE:
<221> NAME/KEY: Xaa
<222> LOCATION: (4)..(5)
<223> OTHER INFORMATION: Thr-Ser pseudoproline protected dipeptide
<220> FEATURE:
<221> NAME/KEY: MISC_FEATURE
<222> LOCATION: (6)..(10)
<223> OTHER INFORMATION: each amino acid optionally contains a side
      chain protecting group
<220> FEATURE:
<221> NAME/KEY: MISC_FEATURE
<222> LOCATION: (12)..(15)
<223> OTHER INFORMATION: each amino acid optionally contains a side
      chain protecting group
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (21)..(22)
```

```
<223> OTHER INFORMATION: each amino acid optionally contains a side
      chain protecting group
<220> FEATURE:
<221> NAME/KEY: MISC_FEATURE
<222> LOCATION: (25)..(26)
<223> OTHER INFORMATION: each amino acid optionally contains a side
      chain protecting group

<400> SEQUENCE: 4

Xaa Thr Phe Xaa Xaa Asp Tyr Ser Lys Tyr Leu Asp Ser Arg Arg Ala
1               5                   10                  15

Gln Asp Phe Val Gln Trp Leu Met Asn Thr
            20                  25

<210> SEQ ID NO 5
<211> LENGTH: 26
<212> TYPE: PRT
<213> ORGANISM: Artificial Sequence
<220> FEATURE:
<223> OTHER INFORMATION: C-terminal peptide with Xmb-Gly and
      pseudoproline pTS and pDS
<220> FEATURE:
<221> NAME/KEY: Xaa
<222> LOCATION: (1)..(1)
<223> OTHER INFORMATION: Xmb-protected glycine
<220> FEATURE:
<221> NAME/KEY: MISC_FEATURE
<222> LOCATION: (2)..(2)
<223> OTHER INFORMATION: optionally contains a side chain protecting
      group
<220> FEATURE:
<221> NAME/KEY: Xaa
<222> LOCATION: (4)..(5)
<223> OTHER INFORMATION: Thr-Ser pseudoproline protected dipeptide
<220> FEATURE:
<221> NAME/KEY: MISC_FEATURE
<222> LOCATION: (6)..(10)
<223> OTHER INFORMATION: each amino acid optionally contains a side
      chain protecting group
<220> FEATURE:
<221> NAME/KEY: Xaa
<222> LOCATION: (12)..(13)
<223> OTHER INFORMATION: Asp-Ser pseudoproline protected dipeptide
<220> FEATURE:
<221> NAME/KEY: MISC_FEATURE
<222> LOCATION: (14)..(15)
<223> OTHER INFORMATION: each amino acid optionally contains a side
      chain protecting group
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (21)..(22)
<223> OTHER INFORMATION: each amino acid optionally contains a side
      chain protecting group
<220> FEATURE:
<221> NAME/KEY: MISC_FEATURE
<222> LOCATION: (25)..(26)
<223> OTHER INFORMATION: each amino acid optionally contains a side
      chain protecting group

<400> SEQUENCE: 5

Xaa Thr Phe Xaa Xaa Asp Tyr Ser Lys Tyr Leu Xaa Xaa Arg Arg Ala
1               5                   10                  15

Gln Asp Phe Val Gln Trp Leu Met Asn Thr
            20                  25

<210> SEQ ID NO 6
<211> LENGTH: 26
<212> TYPE: PRT
```

```
<213> ORGANISM: Artificial Sequence
<220> FEATURE:
<223> OTHER INFORMATION: C-terminal peptide with Xmb-Gly and
      pseudoprolines pYS and pDS
<220> FEATURE:
<221> NAME/KEY: Xaa
<222> LOCATION: (1)..(1)
<223> OTHER INFORMATION: Xmb-protected glycine
<220> FEATURE:
<221> NAME/KEY: MISC_FEATURE
<222> LOCATION: (2)..(2)
<223> OTHER INFORMATION: optionally contains a side chain protecting
      group
<220> FEATURE:
<221> NAME/KEY: MISC_FEATURE
<222> LOCATION: (4)..(6)
<223> OTHER INFORMATION: each amino acid optionally contains a side
      chain protecting group
<220> FEATURE:
<221> NAME/KEY: Xaa
<222> LOCATION: (7)..(8)
<223> OTHER INFORMATION: Tyr-Ser pseudoproline protected dipeptide
<220> FEATURE:
<221> NAME/KEY: MISC_FEATURE
<222> LOCATION: (9)..(10)
<223> OTHER INFORMATION: each amino acid optionally contains a side
      chain protecting group
<220> FEATURE:
<221> NAME/KEY: Xaa
<222> LOCATION: (12)..(13)
<223> OTHER INFORMATION: Asp-Ser pseudoproline protected dipeptide
<220> FEATURE:
<221> NAME/KEY: MISC_FEATURE
<222> LOCATION: (14)..(15)
<223> OTHER INFORMATION: each amino acid optionally contains a side
      chain protecting group
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (20)..(22)
<223> OTHER INFORMATION: each amino acid optionally contains a side
      chain protecting group
<220> FEATURE:
<221> NAME/KEY: MISC_FEATURE
<222> LOCATION: (25)..(26)
<223> OTHER INFORMATION: each amino acid optionally contains a side
      chain protecting group

<400> SEQUENCE: 6

Xaa Thr Phe Thr Ser Asp Xaa Xaa Lys Tyr Leu Xaa Xaa Arg Arg Ala
1               5                   10                  15

Gln Asp Phe Val Gln Trp Leu Met Asn Thr
            20                  25

<210> SEQ ID NO 7
<211> LENGTH: 23
<212> TYPE: PRT
<213> ORGANISM: Artificial Sequence
<220> FEATURE:
<223> OTHER INFORMATION: C-terminal peptide with Xmb-Leu and
      pseudoproline pTS
<220> FEATURE:
<221> NAME/KEY: Xaa
<222> LOCATION: (1)..(2)
<223> OTHER INFORMATION: Thr-Ser pseudoproline protected dipeptide
<220> FEATURE:
<221> NAME/KEY: MISC_FEATURE
<222> LOCATION: (3)..(7)
<223> OTHER INFORMATION: each amino acid optionally contains a side
      chain protecting group
<220> FEATURE:
<221> NAME/KEY: Xaa
```

```
<222> LOCATION: (8)..(8)
<223> OTHER INFORMATION: Xmb-protected leucine
<220> FEATURE:
<221> NAME/KEY: MISC_FEATURE
<222> LOCATION: (9)..(12)
<223> OTHER INFORMATION: each amino acid optionally contains a side
      chain protecting group
<220> FEATURE:
<221> NAME/KEY: MISC_FEATURE
<222> LOCATION: (14)..(15)
<223> OTHER INFORMATION: each amino acid optionally contains a side
      chain protecting group
<220> FEATURE:
<221> NAME/KEY: MISC_FEATURE
<222> LOCATION: (18)..(19)
<223> OTHER INFORMATION: each amino acid optionally contains a side
      chain protecting group
<220> FEATURE:
<221> NAME/KEY: MISC_FEATURE
<222> LOCATION: (22)..(23)
<223> OTHER INFORMATION: each amino acid optionally contains a side
      chain protecting group

<400> SEQUENCE: 7

Xaa Xaa Asp Tyr Ser Lys Tyr Xaa Asp Ser Arg Arg Ala Gln Asp Phe
1               5                   10                  15

Val Gln Trp Leu Met Asn Thr
            20

<210> SEQ ID NO 8
<211> LENGTH: 20
<212> TYPE: PRT
<213> ORGANISM: Artificial Sequence
<220> FEATURE:
<223> OTHER INFORMATION: C-terminal peptide with Xmb-Leu and
      pseudoproline pYS
<220> FEATURE:
<221> NAME/KEY: Xaa
<222> LOCATION: (1)..(2)
<223> OTHER INFORMATION: Tyr-Ser pseudoproline protected dipeptide
<220> FEATURE:
<221> NAME/KEY: MISC_FEATURE
<222> LOCATION: (3)..(4)
<223> OTHER INFORMATION: each amino acid optionally contains a side
      chain protecting group
<220> FEATURE:
<221> NAME/KEY: Xaa
<222> LOCATION: (5)..(5)
<223> OTHER INFORMATION: Xmb-protected leucine
<220> FEATURE:
<221> NAME/KEY: MISC_FEATURE
<222> LOCATION: (6)..(9)
<223> OTHER INFORMATION: each amino acid optionally contains a side
      chain protecting group
<220> FEATURE:
<221> NAME/KEY: MISC_FEATURE
<222> LOCATION: (11)..(12)
<223> OTHER INFORMATION: each amino acid optionally contains a side
      chain protecting group
<220> FEATURE:
<221> NAME/KEY: MISC_FEATURE
<222> LOCATION: (15)..(16)
<223> OTHER INFORMATION: each amino acid optionally contains a side
      chain protecting group
<220> FEATURE:
<221> NAME/KEY: MISC_FEATURE
<222> LOCATION: (19)..(20)
<223> OTHER INFORMATION: each amino acid optionally contains a side
      chain protecting group
```

<400> SEQUENCE: 8

Xaa Xaa Lys Tyr Xaa Asp Ser Arg Arg Ala Gln Asp Phe Val Gln Trp
1               5                   10                  15

Leu Met Asn Thr
            20

<210> SEQ ID NO 9
<211> LENGTH: 15
<212> TYPE: PRT
<213> ORGANISM: Artificial Sequence
<220> FEATURE:
<223> OTHER INFORMATION: C-terminal peptide with Xmb-Ala and
      pseudoproline pDS
<220> FEATURE:
<221> NAME/KEY: Xaa
<222> LOCATION: (1)..(2)
<223> OTHER INFORMATION: Asp-Ser pseudoproline protected dipeptide
<220> FEATURE:
<221> NAME/KEY: MISC_FEATURE
<222> LOCATION: (3)..(4)
<223> OTHER INFORMATION: each amino acid optionally contains a side
      chain protecting group
<220> FEATURE:
<221> NAME/KEY: Xaa
<222> LOCATION: (5)..(5)
<223> OTHER INFORMATION: Xmb-protected alanine
<220> FEATURE:
<221> NAME/KEY: MISC_FEATURE
<222> LOCATION: (6)..(7)
<223> OTHER INFORMATION: each amino acid optionally contains a side
      chain protecting group
<220> FEATURE:
<221> NAME/KEY: MISC_FEATURE
<222> LOCATION: (10)..(11)
<223> OTHER INFORMATION: each amino acid optionally contains a side
      chain protecting group
<220> FEATURE:
<221> NAME/KEY: MISC_FEATURE
<222> LOCATION: (14)..(15)
<223> OTHER INFORMATION: each amino acid optionally contains a side
      chain protecting group

<400> SEQUENCE: 9

Xaa Xaa Arg Arg Xaa Gln Asp Phe Val Gln Trp Leu Met Asn Thr
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: C-terminal peptide with Xmb-Ala and
      pseudoproline pYS
<220> FEATURE:
<221> NAME/KEY: Xaa
<222> LOCATION: (1)..(2)
<223> OTHER INFORMATION: Tyr-Ser pseudoproline protected dipeptide
<220> FEATURE:
<221> NAME/KEY: MISC_FEATURE
<222> LOCATION: (3)..(4)
<223> OTHER INFORMATION: each amino acid optionally contains a side
      chain protecting group
<220> FEATURE:
<221> NAME/KEY: MISC_FEATURE
<222> LOCATION: (6)..(9)
<223> OTHER INFORMATION: each amino acid optionally contains a side
      chain protecting group
<220> FEATURE:
<221> NAME/KEY: Xaa
<222> LOCATION: (10)..(10)
<223> OTHER INFORMATION: Xmb-protected alanine
<220> FEATURE:
<221> NAME/KEY: MISC_FEATURE

```
<222> LOCATION: (11)..(12)
<223> OTHER INFORMATION: each amino acid optionally contains a side
      chain protecting group
<220> FEATURE:
<221> NAME/KEY: MISC_FEATURE
<222> LOCATION: (15)..(16)
<223> OTHER INFORMATION: each amino acid optionally contains a side
      chain protecting group
<220> FEATURE:
<221> NAME/KEY: MISC_FEATURE
<222> LOCATION: (19)..(20)
<223> OTHER INFORMATION: each amino acid optionally contains a side
      chain protecting group

<400> SEQUENCE: 10

Xaa Xaa Lys Tyr Leu Asp Ser Arg Arg Xaa Gln Asp Phe Val Gln Trp
1               5                   10                  15

Leu Met Asn Thr
            20

<210> SEQ ID NO 11
<211> LENGTH: 23
<212> TYPE: PRT
<213> ORGANISM: Artificial Sequence
<220> FEATURE:
<223> OTHER INFORMATION: C-terminal peptide with Xmb-Ala and
      pseudoproline pTS
<220> FEATURE:
<221> NAME/KEY: Xaa
<222> LOCATION: (1)..(2)
<223> OTHER INFORMATION: Thr-Ser pseudoproline protected dipeptide
<220> FEATURE:
<221> NAME/KEY: MISC_FEATURE
<222> LOCATION: (3)..(7)
<223> OTHER INFORMATION: each amino acid optionally contains a side
      chain protecting group
<220> FEATURE:
<221> NAME/KEY: MISC_FEATURE
<222> LOCATION: (9)..(12)
<223> OTHER INFORMATION: each amino acid optionally contains a side
      chain protecting group
<220> FEATURE:
<221> NAME/KEY: Xaa
<222> LOCATION: (13)..(13)
<223> OTHER INFORMATION: Xmb-protected alanine
<220> FEATURE:
<221> NAME/KEY: MISC_FEATURE
<222> LOCATION: (14)..(15)
<223> OTHER INFORMATION: each amino acid optionally contains a side
      chain protecting group
<220> FEATURE:
<221> NAME/KEY: MISC_FEATURE
<222> LOCATION: (18)..(19)
<223> OTHER INFORMATION: each amino acid optionally contains a side
      chain protecting group
<220> FEATURE:
<221> NAME/KEY: MISC_FEATURE
<222> LOCATION: (22)..(23)
<223> OTHER INFORMATION: each amino acid optionally contains a side
      chain protecting group

<400> SEQUENCE: 11

Xaa Xaa Asp Thr Ser Lys Tyr Leu Asp Ser Arg Arg Xaa Gln Asp Phe
1               5                   10                  15

Val Gln Trp Leu Met Asn Thr
            20

<210> SEQ ID NO 12
<211> LENGTH: 29
<212> TYPE: PRT
<213> ORGANISM: Artificial Sequence
```

-continued

```
<220> FEATURE:
<223> OTHER INFORMATION: glucagon sequence with Xmb-Gly and
      pseudoproline pDS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: Xaa
<222> LOCATION: (4)..(4)
<223> OTHER INFORMATION: Xmb-protected glycine
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: MISC_FEATURE
<222> LOCATION: (7)..(13)
<223> OTHER INFORMATION: each amino acid optionally contains a side
      chain protecting group
<220> FEATURE:
<221> NAME/KEY: Xaa
<222> LOCATION: (15)..(16)
<223> OTHER INFORMATION: Asp-Ser pseudoproline protected dipeptide
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 12

His Ser Gln Xaa Thr Phe Thr Ser Asp Tyr Ser Lys Tyr Leu Xaa Xaa
1               5                   10                  15

Arg Arg Ala Gln Asp Phe Val Gln Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: glucagon sequence with Xmb-Gly and
      pseudoproline pYS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: Xaa
<222> LOCATION: (4)..(4)
<223> OTHER INFORMATION: Xmb-protected glycine
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: MISC_FEATURE
```

```
<222> LOCATION: (7)..(9)
<223> OTHER INFORMATION: each amino acid optionally contains a side
      chain protecting group
<220> FEATURE:
<221> NAME/KEY: Xaa
<222> LOCATION: (10)..(11)
<223> OTHER INFORMATION: Tyr-Ser pseudoproline protected dipeptide
<220> FEATURE:
<221> NAME/KEY: MISC_FEATURE
<222> LOCATION: (12)..(13)
<223> OTHER INFORMATION: each amino acid optionally contains a side
      chain protecting group
<220> FEATURE:
<221> NAME/KEY: MISC_FEATURE
<222> LOCATION: (15)..(18)
<223> OTHER INFORMATION: each amino acid optionally contains a side
      chain protecting group
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 13

His Ser Gln Xaa Thr Phe Thr Ser Asp Xaa Xaa Lys Tyr Leu Asp Ser
1               5                   10                  15

Arg Arg Ala Gln Asp Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: glucagon sequence with Xmb-Gly and
      pseudoproline pTS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: Xaa
<222> LOCATION: (4)..(4)
<223> OTHER INFORMATION: Xmb-protected glycine
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: Xaa
<222> LOCATION: (7)..(8)
<223> OTHER INFORMATION: Thr-Ser pseudoproline protected dipeptide
<220> FEATURE:
<221> NAME/KEY: MISC_FEATURE
<222> LOCATION: (9)..(13)
<223> OTHER INFORMATION: each amino acid optionally contains a side
      chain protecting group
<220> FEATURE:
<221> NAME/KEY: MISC_FEATURE
<222> LOCATION: (15)..(18)
<223> OTHER INFORMATION: each amino acid optionally contains a side
      chain protecting group
<220> FEATURE:
<221> NAME/KEY: MISC_FEATURE
```

-continued

```
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 14

His Ser Gln Xaa Thr Phe Xaa Xaa Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: glucagon sequence with Xmb-Gly and
      pseudoprolines pTS and pDS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: Xaa
<222> LOCATION: (4)..(4)
<223> OTHER INFORMATION: Xmb-protected glycine
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: Xaa
<222> LOCATION: (7)..(8)
<223> OTHER INFORMATION: Thr-Ser pseudoproline protected dipeptide
<220> FEATURE:
<221> NAME/KEY: MISC_FEATURE
<222> LOCATION: (9)..(13)
<223> OTHER INFORMATION: each amino acid optionally contains a side
      chain protecting group
<220> FEATURE:
<221> NAME/KEY: Xaa
<222> LOCATION: (15)..(16)
<223> OTHER INFORMATION: Asp-Ser pseudoproline protected dipeptide
<220> FEATURE:
<221> NAME/KEY: MISC_FEATURE
<222> LOCATION: (18)..(19)
<223> OTHER INFORMATION: each amino acid optionally contains a side
      chain protecting group
<220> FEATURE:
<221> NAME/KEY: MISC_FEATURE
<222> LOCATION: (21)..(22)
<223> OTHER INFORMATION: each amino acid optionally contains a side
      chain protecting group
<220> FEATURE:
<221> NAME/KEY: MISC_FEATURE
<222> LOCATION: (25)..(26)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group
```

<400> SEQUENCE: 15

His Ser Gln Xaa Thr Phe Xaa Xaa Asp Tyr Ser Lys Tyr Leu Xaa Xaa
1               5                   10                  15

Arg Arg Ala Gln Asp Phe Val Gln Trp Leu Met Asn Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: glucagon sequence with Xmb-Gly and
      pseudoprolines pYS and pDS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: Xaa
<222> LOCATION: (4)..(4)
<223> OTHER INFORMATION: Xmb-protected glycine
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: MISC_FEATURE
<222> LOCATION: (7)..(9)
<223> OTHER INFORMATION: each amino acid optionally contains a side
      chain protecting group
<220> FEATURE:
<221> NAME/KEY: Xaa
<222> LOCATION: (10)..(11)
<223> OTHER INFORMATION: Tyr-Ser pseudoproline protected dipeptide
<220> FEATURE:
<221> NAME/KEY: MISC_FEATURE
<222> LOCATION: (12)..(13)
<223> OTHER INFORMATION: each amino acid optionally contains a side
      chain protecting group
<220> FEATURE:
<221> NAME/KEY: Xaa
<222> LOCATION: (15)..(16)
<223> OTHER INFORMATION: Asp-Ser pseudoproline protected dipeptide
<220> FEATURE:
<221> NAME/KEY: MISC_FEATURE
<222> LOCATION: (17)..(18)
<223> OTHER INFORMATION: each amino acid optionally contains a side
      chain protecting group
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (23)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 16

His Ser Gln Xaa Thr Phe Thr Ser Asp Xaa Xaa Lys Tyr Leu Xaa Xaa
1               5                   10                  15

Arg Arg Ala Gln Asp Phe Val Gln Trp Leu Met Asn Thr
            20                  25

```
<210> SEQ ID NO 17
<211> LENGTH: 29
<212> TYPE: PRT
<213> ORGANISM: Artificial Sequence
<220> FEATURE:
<223> OTHER INFORMATION: glucagon sequence with Xmb-Leu and
      pseudoproline pTS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: Xaa
<222> LOCATION: (7)..(8)
<223> OTHER INFORMATION: Thr-Ser pseudoproline protected dipeptide
<220> FEATURE:
<221> NAME/KEY: MISC_FEATURE
<222> LOCATION: (9)..(13)
<223> OTHER INFORMATION: each amino acid optionally contains a side
      chain protecting group
<220> FEATURE:
<221> NAME/KEY: Xaa
<222> LOCATION: (14)..(14)
<223> OTHER INFORMATION: Xmb-protected leucine
<220> FEATURE:
<221> NAME/KEY: MISC_FEATURE
<222> LOCATION: (15)..(18)
<223> OTHER INFORMATION: each amino acid optionally contains a side
      chain protecting group
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 17

His Ser Gln Gly Thr Phe Xaa Xaa Asp Tyr Ser Lys Tyr Xaa Asp Ser
1               5                   10                  15

Arg Arg Ala Gln Asp Phe Val Gln Trp Leu Met Asn Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: glucagon sequence with Xmb-Leu and
      pseudoproline pYS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: MISC_FEATURE
```

```
<222> LOCATION: (7)..(9)
<223> OTHER INFORMATION: each amino acid optionally contains a side
      chain protecting group
<220> FEATURE:
<221> NAME/KEY: Xaa
<222> LOCATION: (10)..(11)
<223> OTHER INFORMATION: Tyr-Ser pseudoproline protected dipeptide
<220> FEATURE:
<221> NAME/KEY: MISC_FEATURE
<222> LOCATION: (12)..(13)
<223> OTHER INFORMATION: each amino acid optionally contains a side
      chain protecting group
<220> FEATURE:
<221> NAME/KEY: Xaa
<222> LOCATION: (14)..(14)
<223> OTHER INFORMATION: Xmb-protected leucine
<220> FEATURE:
<221> NAME/KEY: MISC_FEATURE
<222> LOCATION: (15)..(18)
<223> OTHER INFORMATION: each amino acid optionally contains a side
      chain protecting group
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 18

His Ser Gln Gly Thr Phe Thr Ser Asp Xaa Xaa Lys Tyr Xaa Asp Ser
1               5                   10                  15

Arg Arg Ala Gln Asp Phe Val Gln Trp Leu Met Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: glucagon sequence with Xmb-Ala and
      pseudoproline pDS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: MISC_FEATURE
<222> LOCATION: (5)..(5)
<223> OTHER INFORMATION: each amino acid optionally contains a side
      chain protecting group
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: MISC_FEATURE
<222> LOCATION: (7)..(13)
<223> OTHER INFORMATION: each amino acid optionally contains a side
      chain protecting group
<220> FEATURE:
<221> NAME/KEY: Xaa
<222> LOCATION: (15)..(16)
<223> OTHER INFORMATION: Asp-Ser pseudoproline protected dipeptide
<220> FEATURE:
<221> NAME/KEY: MISC_FEATURE
```

```
<222> LOCATION: (17)..(18)
<223> OTHER INFORMATION: each amino acid optionally contains a side
      chain protecting group
<220> FEATURE:
<221> NAME/KEY: Xaa
<222> LOCATION: (19)..(19)
<223> OTHER INFORMATION: Xmb-protected alanine
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 19

His Ser Gln Gly Thr Phe Thr Ser Asp Tyr Ser Lys Tyr Leu Xaa Xaa
1               5                   10                  15

Arg Arg Xaa Gln Asp Phe Val Gln Trp Leu Met Asn Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: glucagon sequence with Xmb-Gly, Xmb-Ala and
      pseudoproline pYS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: Xaa
<222> LOCATION: (4)..(4)
<223> OTHER INFORMATION: Xmb-protected glycine
<220> FEATURE:
<221> NAME/KEY: MISC_FEATURE
<222> LOCATION: (5)..(5)
<223> OTHER INFORMATION: each amino acid optionally contains a side
      chain protecting group
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: MISC_FEATURE
<222> LOCATION: (7)..(9)
<223> OTHER INFORMATION: each amino acid optionally contains a side
      chain protecting group
<220> FEATURE:
<221> NAME/KEY: Xaa
<222> LOCATION: (10)..(11)
<223> OTHER INFORMATION: Tyr-Ser pseudoproline protected dipeptide
<220> FEATURE:
<221> NAME/KEY: MISC_FEATURE
<222> LOCATION: (12)..(13)
<223> OTHER INFORMATION: each amino acid optionally contains a side
      chain protecting group
<220> FEATURE:
<221> NAME/KEY: MISC_FEATURE
<222> LOCATION: (15)..(18)
<223> OTHER INFORMATION: each amino acid optionally contains a side
      chain protecting group
<220> FEATURE:
<221> NAME/KEY: Xaa
```

```
<222> LOCATION: (19)..(19)
<223> OTHER INFORMATION: Xmb-protected alanine
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group

<400> SEQUENCE: 20

His Ser Gln Xaa Thr Phe Thr Ser Asp Xaa Xaa Lys Tyr Leu Asp Ser
1               5                   10                  15

Arg Arg Xaa Gln Asp Phe Val Gln Trp Leu Met Asn Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: glucagon sequence with Xmb-Ala and
      pseudoproline pTS
<220> FEATURE:
<221> NAME/KEY: MISC_FEATURE
<222> LOCATION: (1)..(3)
<223> OTHER INFORMATION: each amino acid optionally contains a side
      chain protecting group
<220> FEATURE:
<221> NAME/KEY: MISC_FEATURE
<222> LOCATION: (5)..(5)
<223> OTHER INFORMATION: optionally contains a side chain protecting
      group
<220> FEATURE:
<221> NAME/KEY: Xaa
<222> LOCATION: (7)..(8)
<223> OTHER INFORMATION: Thr-Ser pseudoproline protected dipeptide
<220> FEATURE:
<221> NAME/KEY: MISC_FEATURE
<222> LOCATION: (9)..(13)
<223> OTHER INFORMATION: each amino acid optionally contains a side
      chain protecting group
<220> FEATURE:
<221> NAME/KEY: MISC_FEATURE
<222> LOCATION: (15)..(18)
<223> OTHER INFORMATION: each amino acid optionally contains a side
      chain protecting group
<220> FEATURE:
<221> NAME/KEY: Xaa
<222> LOCATION: (19)..(19)
<223> OTHER INFORMATION: Xmb-protected alanine
<220> FEATURE:
<221> NAME/KEY: MISC_FEATURE
<222> LOCATION: (20)..(21)
<223> OTHER INFORMATION: each amino acid optionally contains a side
      chain protecting group
<220> FEATURE:
<221> NAME/KEY: MISC_FEATURE
<222> LOCATION: (24)..(25)
<223> OTHER INFORMATION: each amino acid optionally contains a side
      chain protecting group
<220> FEATURE:
<221> NAME/KEY: MISC_FEATURE
<222> LOCATION: (28)..(29)
<223> OTHER INFORMATION: each amino acid optionally contains a side
      chain protecting group
```

```
<400> SEQUENCE: 21

His Ser Gln Gly Thr Phe Xaa Xaa Asp Tyr Ser Lys Tyr Leu Asp Ser
1               5                   10                  15

Arg Arg Xaa Gln Asp Phe Val Gln Trp Leu Met Asn Thr
            20                  25
```

PROCESS FOR THE PREPARATION OF HIGH PURITY GLUCAGON

CROSS-REFERENCE TO RELATED APPLICATIONS

This patent application claims the benefit of European Patent Application No. 19180871.6, filed on Jun. 18, 2019, the disclosure of which is incorporated herein by reference in its entirety for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 27,562 Byte ASCII (Text) file named "749583_ST25.TXT," created on Jun. 17, 2020.

FIELD OF THE INVENTION

The present invention provides an improved process for the preparation of high purity glucagon and related intermediates.

BACKGROUND OF THE INVENTION

Glucagon is a polypeptide hormone, secreted by the α-cells of the pancreatic islets of Langerhans. Glucagon is a single chain peptide consisting of 29 natural amino acids (SEQ ID NO: 1, glucagon 1-29) and is represented by the chemical structure shown below Glucagon was first discovered in 1923 by the chemists Kimball and Murlin in the pancreatic extract. Glucagon is indicated for the treatment of severe hypoglycemic reactions which may occur in the management of insulin treated patients or patients with diabetes mellitus.

Earliest isolation of glucagon was from the pancreatic extracts. The extraction from pancreas is difficult and the product is largely contaminated with insulin. The process produces low yield and therefore a large amount of pancreas is required. Moreover, the glucagon of animal origin may induce allergic reactions in some patients making it unsuitable for these patients.

Currently glucagon is produced by recombinant DNA technology or by using Solid Phase Peptide Synthesis (SPPS). Several patents such as U.S. Pat. Nos. 4,826,763 or 6,110,703 describe the synthesis of glucagon using recombinant DNA technology or genetically modified yeast cells.

Recombinant technology, besides being extremely expensive is also an industrially complicated process. It requires the use of specialised equipment, modified organisms during synthesis and elaborate analytical and purification procedures. Apart from the high cost, the biotechnology processes for the production of bio-molecules also suffers from low reproducibility.

These disadvantages suggest that there is a need to develop a low cost, safe, fast and reproducible method for the production of glucagon.

The solid phase peptide synthesis process for glucagon is relatively difficult as the long peptide chains often suffer from on-resin aggregation phenomena due to inter- and intra-molecular hydrogen bonding which leads to several truncated sequences appearing as impurities, reducing both the yield and purity of the final compound.

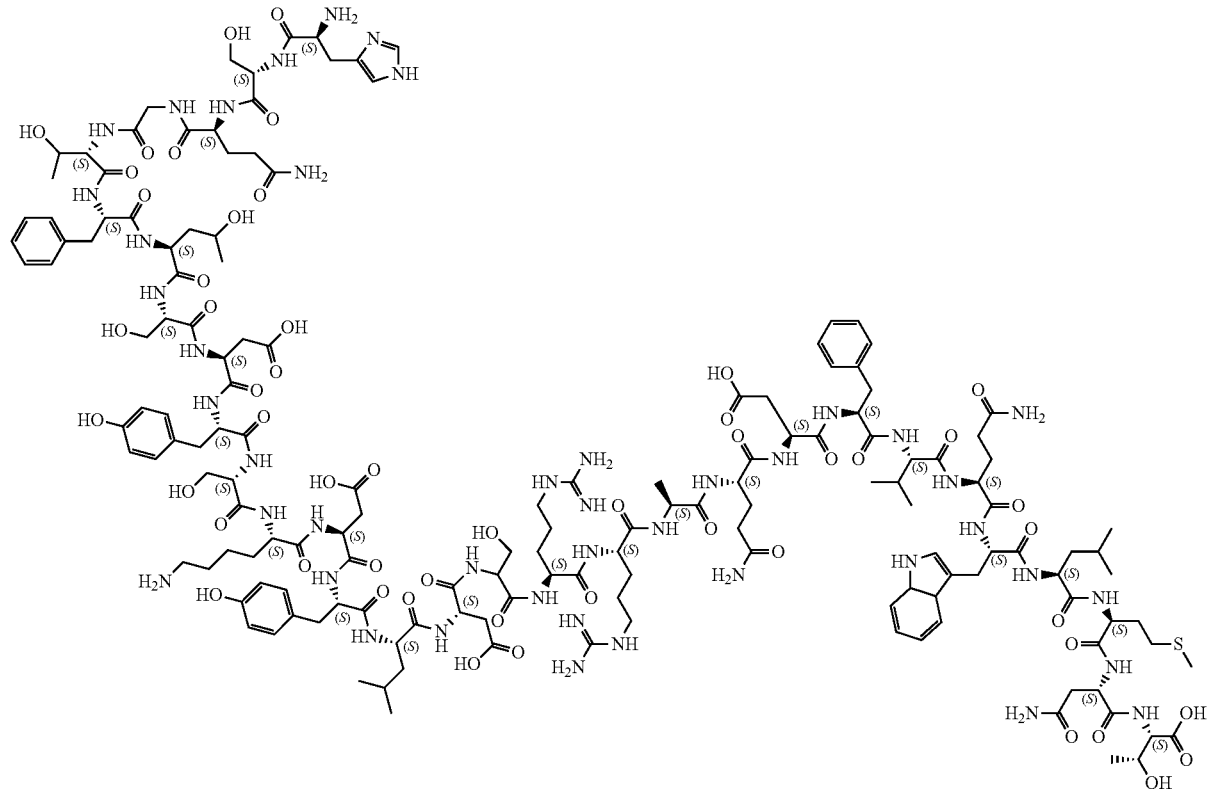

The U.S. Pat. No. 3,642,763 describes the synthesis of glucagon by condensation of 1-6 and 7-29 fragments in the presence of N-hydroxy-succinimide or N-hydroxypthalimide and subsequent splitting of protecting groups in the presence of trifluoroacetic acid. This document does not disclose the purity of the compound obtained in such a process.

The Chinese patent application CN103333239 describes a process for the solid phase peptide synthesis of glucagon wherein the condensation of amino acids is carried out at higher temperatures and wherein the use of pseudoproline dipeptides as protecting groups is disclosed. However, the purity of the glucagon obtained via the described process is consistently low.

Therefore, there exists a need for an improved process for the synthesis of glucagon which provides the product in high yield and purity and which is also cost effective and industrially viable.

OBJECT OF THE INVENTION

It is an objective of the present invention to overcome the above-mentioned drawbacks of the prior art.

It is another objective of the present invention to provide an improved process for the preparation of glucagon, which provides product in high yield as well as high purity.

It is a further objective of the present invention to provide useful intermediates for the synthesis of glucagon.

SUMMARY OF THE INVENTION

The present invention provides an improved process for the preparation of glucagon.

In one embodiment, the invention relates to a process for the preparation of glucagon comprising the use of at least one Xmb-protected amino acid and at least one pseudoproline dipeptide, wherein Xmb is a protecting group selected from, e.g., 2,4,6-trimethoxybenzyl (Tmb), 2,4-dimethoxybenzyl (Dmb) and 2-hydroxy-4-methoxybenzyl (Hmb) group.

In another embodiment, the invention relates to a process for the preparation of glucagon comprising the use of an intermediate C-terminal peptide, which comprises at least one Xmb-protected amino acid and at least one pseudoproline dipeptide, wherein Xmb is as defined above, and wherein the C-terminal peptide is of 2 to 28 amino acids in length, sharing the C-terminal amino acid sequence of glucagon ending at its C-terminal threonine.

A further embodiment of the invention relates to different pseudoproline dipeptides which can be used in the synthesis of glucagon. The pseudoproline dipeptides are preferably selected from:
Fmoc-Asp(OtBu)-Ser[psi(Me, Me)pro]-OH
Fmoc-Asn(Trt)-Thr[psi(Me, Me)pro]-OH
Fmoc-Tyr(tBu)-Ser[psi(Me, Me)pro]-OH
Fmoc-Phe-Thr[psi(Me, Me)pro]-OH and
Fmoc-Thr(tBu)-Ser[psi(Me, Me)pro]-OH.

More preferably, the process for the preparation of glucagon comprises the use of (Tmb)Gly and of Fmoc-Asp(OtBu)-Ser[psi(Me, Me)pro]-OH.

A further embodiment of the present invention relates to various C-terminal peptides and protected glucagon sequences which are intermediates in the preparation of glucagon.

DETAILED DESCRIPTION OF THE INVENTION

The present invention relates to a process for the preparation of glucagon of formula I (SEQ ID NO: 1):

(I)

```
         1                5                  10
    His-Ser-Gln-Gly-Thr-Phe-Thr-Ser-Asp-Tyr- 15                 20
    Ser-Lys-Tyr-Leu-Asp-Ser-Arg-Arg-Ala-Gln- 25                 29
    Asp-Phe-Val-Gln-Trp-Leu-Met-Asn-Thr
``` also indicated by the following sequence of amino acids one-letter codes:

HSQGTFTSDYSKYLDSRRAQDFVQWLMNT.

In the synthesis of large peptide molecules, such as glucagon, the conformation of the growing peptide chain and its physico-chemical properties are of considerable importance. The formation of secondary structures often leads to problems of aggregation causing incomplete coupling reactions, resulting in a decrease in the synthetic yield and purity of the final compound.

For instance, it was found that in a stepwise SPPS preparation of glucagon, after the insertion of Gly4 residue (i.e., glycine in position 4), the coupling efficiency dramatically decreases and an efficient completion of glucagon sequence is hampered. This was demonstrated by the presence of the truncated sequences at the residues Gly4, Gln3 and Ser2 in the crude glucagon (after cleavage from resin) and by its very low HPLC purity (see Example 1, Lot 1A of Experimental Part).

Similarly, intra- and inter-molecular aggregation phenomena may be responsible for a decrease in the efficiency of coupling reactions in the synthesis of glucagon even at an earlier stage in the stepwise elongation, for instance after the insertion of Leu14. To solve this problem, it was surprisingly found that the use of a pseudoproline dipeptide allows to maintain coupling efficiency during peptide elongation in the SPPS preparation of glucagon.

Still, the use of pseudoproline dipeptides is not sufficient to obtain crude glucagon in decent yield (see Example 1, Lot 1B of Experimental Part).

The insertion of N,N-bisprotected amino acids, such as Fmoc(Xmb)-Gly-OH instead of more common Fmoc-Gly-OH, as residue in position 4, followed by selective cleavage of Fmoc group, provides an intermediate C-terminal peptide terminating at Xmb-protected glycine at N-terminal end. Surprisingly, the coupling of such C-terminal peptide with the next amino acid of the glucagon sequence, or a longer peptide according to the glucagon sequence, provides an elongated product with a better yield and purity. Without being bound to this theory, it is assumed that because Xmb, which may be selected from Tmb, Dmb and Hmb groups, causes steric hindrance at the coupling site, it thereby prevents secondary structure formation, and aggregation, but instead makes the glycine amino group available for coupling.

Fmoc(Xmb)-Gly-OH may be selected from Fmoc(Hmb)-Gly-OH, Fmoc(Dmb)-Gly-OH and Fmoc(Tmb)-Gly-OH.

Fmoc(Xmb)-protected glycine is represented below:

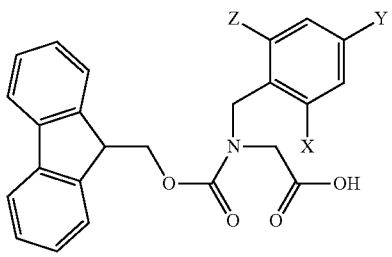

Y = OMe, X = OH, Z = H → Fmoc(Hmb)-Gly-OH
Y, Z = OMe, X = H → Fmoc(Dmb)-Gly-OH
X, Y, Z = OMe → Fmoc(Tmb)-Gly-OH Similarly, the insertion of N,N-bisprotected leucine, such as Fmoc(Xmb)-Leu-OH, instead of common Fmoc-Leu-OH, as residue in position 14 in the preparation of glucagon, as explained above for glycine, may prevent secondary structure formation, resulting in an improved yield and higher quality of the final compound. In addition, or alternatively, N,N-bisprotected alanine, such as Fmoc(Xmb)-Ala-OH, may be inserted as residue in position 19, to similarly prevent aggregation and secondary structure formation.

Thus, the amino acid in the Xmb-protected amino acid is preferably selected from glycine, alanine, and leucine.

The term "N,N-bisprotected amino acid" therefore refers to amino acids, such as glycine, leucine or alanine, which are protected by two protecting groups, a terminal protecting group, for instance Fmoc, and an Xmb protecting group, both at the alpha-amino group. The terminal protecting group is selectively cleaved prior to the coupling of such amino group with the carboxy group of the next amino acid, or peptide, in the glucagon sequence, whereas the Xmb protecting group is maintained during said coupling reaction.

The term "terminal protecting group" as used herein therefore refers to the protecting group for the alpha-amino group of the amino acids or of the peptides used in the preparation of glucagon, which is cleaved prior to the coupling to elongate the peptide sequence. Preferably, the terminal protecting group is 9-fluorenylmethyloxycarbonyl (Fmoc).

The term "Xmb-protected amino acid" refers to amino acids such as glycine, leucine or alanine which are protected at alpha-amino group by 2,4,6-trimethoxybenzyl (Tmb), 2,4-dimethoxybenzyl (Dmb) or 2-hydroxy-4-methoxybenzyl group (Hmb). The Xmb protecting group is cleavable after completion of the peptide elongation by acid treatment, for instance with a mixture comprising TFA.

The amino acids employed in the process of present invention have the natural L-configuration; in general, the amino acids (optionally protected with Fmoc, Xmb or Fmoc (Xmb)) employed in the process of the present invention are commercially available.

The term "resin" is used to describe a functionalized polymeric solid support suitable to perform peptide synthesis (SPPS). Preferably, the resin in the present context may be selected from 2-chlorotrityl chloride (CTC), trityl chloride, Wang, Rink amide, Rink amide AM, and Rink amide MBHA resins.

"On-resin aggregation" refers to the secondary structure formation or clumping of the peptide chain due to intra- and inter-molecular hydrogen bonding interactions which decrease the availability of the peptide to coupling reaction and hinder the further growth of the peptide chain.

The term "pseudoproline" refers to an oxazolidine as simultaneous protection of the alpha-amino group and the side-chain hydroxy group of serine or threonine via cyclization with an aldehyde or ketone, exhibiting structural features similar to a proline (see also T. Haack, M. Mutter, Tetrahedron Lett. 1992, 33, 1589-1592). The pseudoproline dipeptide structure is depicted below, wherein also the position of the Fmoc terminal protecting group is indicated:

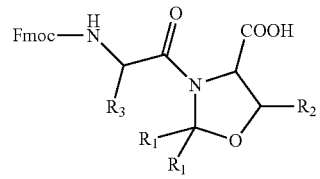

wherein $R_1$ is hydrogen or methyl; $R_2$ is hydrogen for Ser and methyl for Thr; and $R_3$ is the side-chain of the amino acid next to the pseudoproline protected amino acid (configurations at stereocenters are not indicated).

The above pseudoproline dipeptides are also indicated as Fmoc-$A_1$-$A_2$[psi(R1,R1)pro]-OH or more simply as $pA_1A_2$, wherein $A_1$ and $A_2$ is either the three-letter or the one-letter code of the involved amino acid, and wherein, in the context of present invention, $A_1$ refers to aspartic acid, asparagine, tyrosine, phenylalanine or threonine and $A_2$ refers to serine or threonine. In particular, the abbreviation $pA_1A_2$ is used throughout the present disclosure when the pseudoproline dipeptide is incorporated into a peptide sequence, i.e., when it is without the terminal group and the free carboxylic acid at C-terminal end.

The introduction of pseudoproline dipeptides, for instance Fmoc-protected, into a peptide sequence can be performed in the solid-phase under standard coupling conditions. Once the completed peptide is cleaved from the resin by acidolysis, the pseudoproline is also hydrolysed in the same step, providing the two corresponding native amino acids in the sequence. The cleavage of the pseudoproline protection after completion of the peptide elongation occurs by acid treatment, for instance with a mixture comprising TFA.

The pseudoproline dipeptides (protected with a terminal protecting group) employed in the process of the present invention are commercially available.

As used herein, a "side-chain protecting group" is a protecting group for an amino acid side-chain chemical function which is not removed when the terminal protecting group is removed and is stable during coupling reactions. Preferably, side-chain protecting groups are included to protect side-chains of amino acids which are particularly reactive or labile, to avoid side reactions and/or branching of the growing molecule. Illustrative examples include acid-labile protecting groups, as for instance tert-butyloxycarbonyl (Boc), alkyl groups such as tert-butyl (tBu), trityl (Trt), 2,2,4,6,7-pentamethyldihydrobenzofuran-5-sulfonyl (Pbf) and the like. Other protecting groups may be efficiently used as it is apparent to the person skilled in the art.

The criterion for selecting side-chain protecting groups is that generally the protecting group must be stable to the reaction conditions selected for removing the terminal protecting group at each step of the synthesis and has to be removable upon completion of the synthesis of the desired amino acid sequence under reaction conditions that will not alter the peptide chain.

According to what was discussed above, the present invention relates to a process for the preparation of glucagon comprising the use of at least one Xmb-protected amino acid and at least one pseudoproline dipeptide, wherein Xmb is a protecting group selected from, e.g., 2,4,6-trimethoxybenzyl (Tmb), 2,4-dimethoxybenzyl (Dmb), and 2-hydroxy-4-methoxybenzyl (Hmb) group.

In one embodiment, this process for the preparation of glucagon comprises the preparation of a C-terminal peptide of glucagon, wherein the C-terminal peptide is characterized by carrying one or more pseudoproline dipeptides and a Xmb protected N-terminal amino acid.

The term "C-terminal peptide" or "intermediate C-terminal peptide" in the context of present invention refers to a peptide of 2 to 28 amino acids in length, sharing the C-terminal amino acid sequence of glucagon ending with a C-terminal threonine, with reference to glucagon sequence, which has a Thr29 as C-terminal end. The C-terminal peptide may be attached to a resin by its C-terminal end, when glucagon is prepared according to the present invention and by SPPS. It is further defined by having an alpha-amino group capable of reacting with the carboxy group of another amino acid, or peptide at the N-terminal end. Preferably the C-terminal peptide has an Xmb protected N-terminal amino acid.

Preferably the Xmb protecting group is a Tmb protecting group. Preferably the Xmb-protected amino acid is selected from glycine, alanine, and leucine, more preferably glycine. Most preferably the at least one Xmb-protected amino acid is (Tmb)Gly.

In the process described above the C-terminal peptide may be coupled to the subsequent amino acid or subsequent peptide fragment according to the sequence of glucagon.

Preferably, the process for the preparation of glucagon comprises the preparation of the C-terminal peptide by solid phase peptide synthesis comprising the steps of:

a) coupling an alpha-amino-protected amino acid to a resin; and one or more of the steps of:

b) selectively cleaving the terminal protecting group;

c) coupling the subsequent alpha-amino-protected amino acid or peptide to the deprotected amino group obtained in step b) in the presence of a coupling reagent; to obtain the C-terminal peptide of glucagon;

wherein at least one step c) comprises coupling with an alpha-amino-protected-Xmb-protected amino acid, and wherein a further step c) comprises coupling with a pseudoproline dipeptide.

The process for the preparation of glucagon according to the present invention is further characterized by the use of one or more of the different pseudoproline dipeptides.

The pseudoproline dipeptides may be selected from:
Fmoc-Asp(P)-Ser[psi($R_1$, $R_1$)pro]-OH (Fmoc-pDS)
Fmoc-Asn(P)-Thr[psi($R_1$, $R_1$)pro]-OH (Fmoc-pNT)
Fmoc-Tyr(P)-Ser[psi($R_1$, $R_1$)pro]-OH (Fmoc-pYS)
Fmoc-Phe-Thr[psi($R_1$, $R_1$)pro]-OH (Fmoc-pFT) and
Fmoc-Thr(P)-Ser[psi($R_1$, $R_1$)pro]-OH (Fmoc-pTS),
wherein P is a side-chain protecting group or is absent, and R1 is hydrogen or methyl (Me).

Preferably, the pseudoproline dipeptides are selected from:
Fmoc-Asp(OtBu)-Ser[psi(Me, Me)pro]-OH
Fmoc-Asn(Trt)-Thr[psi(Me, Me)pro]-OH
Fmoc-Tyr(tBu)-Ser[psi(Me, Me)pro]-OH
Fmoc-Phe-Thr[psi(Me, Me)pro]-OH and
Fmoc-Thr(tBu)-Ser[psi(Me, Me)pro]-OH.

In a preferred embodiment, Fmoc-Asp(OtBu)-Ser[psi(Me, Me)pro]-OH is used in the synthesis of glucagon according to the present invention.

It is a preferred embodiment, wherein the process according to the invention is characterized by the use of at least one of the C-terminal peptides listed below. A further embodiment of the present invention relates to the intermediate C-terminal peptides themselves, which may be selected from:

```
                                              (SEQ ID NO: 2)
(Xmb)Gly-Thr(P)-Phe-Thr(P)-Ser(P)-Asp(P)-Tyr(P)-

Ser(P)-Lys(P)-Tyr(P)-Leu-pDS-Arg(P)-Arg(P)-Ala-

Gln(P)-Asp(P)-Phe-Val-Gln(P)-Trp(P)-Leu-Met-

Asn(P)-Thr(P), (SEQ ID NO: 3)
(Xmb)Gly-Thr(P)-Phe-Thr(P)-Ser(P)-Asp(P)-pYS-

Lys(P)-Tyr(P)-Leu-Asp(P)-Ser(P)-Arg(P)-Arg(P)-

Ala-Gln(P)-Asp(P)-Phe-Val-Gln(P)-Trp(P)-Leu-Met-

Asn(P)-Thr(P), (SEQ ID NO: 4)
(Xmb)Gly-Thr(P)-Phe-pTS-Asp(P)-Tyr(P)-Ser(P)-

Lys(P)-Tyr(P)-Leu-Asp(P)-Ser(P)-Arg(P)-Arg(P)-

Ala-Gln(P)-Asp(P)-Phe-Val-Gln(P)-Trp(P)-Leu-Met-

Asn(P)-Thr(P), (SEQ ID NO: 5)
(Xmb)Gly-Thr(P)-Phe-pTS-Asp(P)-Tyr(P)-Ser(P)-

Lys(P)-Tyr(P)-Leu-pDS-Arg(P)-Arg(P)-Ala-Gln(P)-

Asp(P)-Phe-Val-Gln(P)-Trp(P)-Leu-Met-Asn(P)-

Thr(P), (SEQ ID NO: 6)
(Xmb)Gly-Thr(P)-Phe-Thr(P)-Ser(P)-Asp(P)-pYS-

Lys(P)-Tyr(P)-Leu-pDS-Arg(P)-Arg(P)-Ala-Gln(P)-

Asp(P)-Phe-Val(P)-Gln(P)-Trp(P)-Leu-Met-Asn(P)-

Thr(P), (SEQ ID NO: 7)
pTS-Asp(P)-Tyr(P)-Ser(P)-Lys(P)-Tyr(P)-(Xmb)Leu-

Asp(P)-Ser(P)-Arg(P)-Arg(P)-Ala-Gln(P)-Asp(P)-

Phe-Val-Gln(P)-Trp(P)-Leu-Met-Asn(P)-Thr(P), (SEQ ID NO: 8)
pYS-Lys(P)-Tyr(P)-(Xmb)Leu-Asp(P)-Ser(P)-

Arg(P)-Arg(P)-Ala-Gln(P)-Asp(P)-Phe-Val-Gln(P)-

Trp(P)-Leu-Met-Asn(P)-Thr(P), (SEQ ID NO: 9)
pDS-Arg(P)-Arg(P)-(Xmb)Ala-Gln(P)-Asp(P)-Phe-

Val-Gln(P)-Trp(P)-Leu-Met-Asn(P)-Thr(P),
```

-continued (SEQ ID NO: 10)
pYS-Lys(P)-Tyr(P)-Leu-Asp(P)-Ser(P)-Arg(P)-

Arg(P)-(Xmb)Ala-Gln(P)-Asp(P)-Phe-Val-Gln(P)-

Trp(P)-Leu-Met-Asn(P)-Thr(P),
and (SEQ ID NO: 11)
pTS-Asp(P)-Tyr(P)-Ser(P)-Lys(P)-Tyr(P)-Leu- Asp(P)-Ser(P)-Arg(P)-Arg(P)-(Xmb)Ala-Gln(P)-

Asp(P)-Phe-Val-Gln(P)-Trp(P)-Leu-Met-Asn(P)-

Thr(P), wherein Xmb is selected from Tmb, Dmb, and Hmb, P is a side-chain protecting group or is absent, and $pA_1A_2$ is a pseudoproline dipeptide as defined above.

In a preferred embodiment, the above defined C-terminal peptides are attached to a solid support at their C-terminal end, more preferably to a Wang resin.

Preferably, the above defined C-terminal peptides are prepared using SPPS by stepwise coupling of amino acids or peptides according to required sequence to the resin using at least one of a coupling reagent and an additive, and elongating the sequence by common SPPS cycles requiring alternate deprotection of the terminal protecting group and coupling steps (or coupling reactions).

The resin is initially activated by the removal of a protecting group. The activated resin is coupled with the first amino acid, i.e., with Thr29, wherein the amino acid is protected by a terminal protecting group and optionally a side-chain protecting group.

The terminal protecting group, which is preferably the Fmoc group, can be removed by treatment with a base. The base may be an inorganic or organic base. Preferably the base is an organic base selected from the group comprising piperidine, pyrrolidine, piperazine, tert-butylamine, DBU and diethylamine, preferably piperidine.

The coupling reaction of amino acids takes place preferably in the presence of a coupling reagent. The coupling reagent may be selected from, among others, e.g., N,N'-diisopropylcarbodiimide (DIC), N,N'-dicyclohexylcarbodiimide (DCC), (Benzotriazol-1-yloxy)tripyrrolidinophosphonium hexafluorophosphate (PyBOP), N,N,N',N'-Tetramethyl-O-(benzotriazol-1-yl)uronium tetrafluoroborate (TBTU), 2-(7-Aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), and ethyl-dimethylaminopropyl carbodiimide (EDC), etc. Preferably, the reaction is carried out in the presence N,N'-diisopropylcarbodiimide.

In a preferred aspect of present invention, the coupling steps are performed also in the presence of an additive. The presence of an additive, when used in the coupling reaction, reduces loss of configuration at the carboxylic acid residue, increases coupling rates and reduces the risk of racemization. The additive may be selected from the group comprising 1-hydroxybenzotriazole (HOBt), 2-hydroxypyridine N-oxide, N-hydroxysuccinimide, 1-hydroxy-7-azabenzotriazole (HOAt), endo-N-hydroxy-5-norbornene-2,3-dicarboxamide and ethyl 2-cyano-2-hydroxyimino-acetate (Oxyma-Pure). Preferably, the reaction is carried out in the presence ethyl 2-cyano-2-hydroxyimino-acetate.

The coupling reaction may be carried out in the presence of a base selected from tertiary amines comprising diisopropylethylamine (DIEA), triethylamine, N-methylmorpholine, N-methylpiperidine, etc; preferably, the reaction is carried out in the presence of DIEA.

The coupling reaction, either involving fragments or amino acids, takes place in the presence of a solvent selected from the group comprising dimethylformamide, dimethyl acetamide, dimethylsulfoxide, dichloromethane, chloroform, tetrahydrofuran, 2-methyl tetrahydrofuran and N-methyl pyrrolidine.

Additionally, the unreacted sites on the resin are optionally capped, to avoid truncated sequences and to prevent any side reactions, by a short treatment with a large excess of a highly reactive unhindered reagent, which is chosen according to the unreacted sites to be capped, and according to well-known peptide synthesis techniques.

Preferably, the intermediate C-terminal peptide for the preparation of glucagon is selected from:

(SEQ ID NO: 2)
(Xmb)Gly-Thr(P)-Phe-Thr(P)-Ser(P)-Asp(P)-Tyr(P)-

Ser(P)-Lys(P)-Tyr(P)-Leu-pDS-Arg(P)-Arg(P)-Ala-

Gln(P)-Asp(P)-Phe-Val-Gln(P)-Trp(P)-Leu-Met-

Asn(P)-Thr(P),
and (SEQ ID NO: 6)
(Xmb)Gly-Thr(P)-Phe-Thr(P)-Ser(P)-Asp(P)-pYS-

Lys(P)-Tyr(P)-Leu-pDS-Arg(P)-Arg(P)-Ala-Gln(P)-

Asp(P)-Phe-Val(P)-Gln(P)-Trp(P)-Leu-Met-Asn(P)-

Thr(P), wherein Xmb, P and $pA_1A_2$ are as defined above. The Xmb is preferably Tmb.

Most preferably the intermediate C-terminal peptide for the preparation of glucagon is:

(SEQ ID NO: 2)
(Tmb)Gly-Thr(tBu)-Phe-Thr(tBu)-Ser(tBu)-Asp(tBu)-

Tyr(tBu)-Ser(tBu)-Lys(Boc)-Tyr(tBu)-Leu-pDS-

Arg(Pbf)-Arg(Pbf)-Ala-Gln(Trt)-Asp(tBu)-Phe-Val-

Gln(Trt)-Trp(Boc)-Leu-Met-Asn(Trt)-Thr(tBu), wherein pDS is Asp(OtBu)-Ser[psi(Me, Me)pro].

In yet another aspect, the invention relates to various optionally protected glucagon sequences or fragments which are intermediates in the synthesis of glucagon. The peptide sequences may be selected from:

(SEQ ID NO: 12)
His(P)-Ser(P)-Gln(P)-(Xmb)Gly-Thr(P)-Phe-Thr(P)-

Ser(P)-Asp(P)-Tyr(P)-Ser(P)-Lys(P)-Tyr(P)-Leu-pDS-

Arg(P)-Arg(P)-Ala-Gln(P)-Asp(P)-Phe-Val-Gln(P)-

Trp(P)-Leu-Met-Asn(P)-Thr(P), (SEQ ID NO: 13)
His(P)-Ser(P)-Gln(P)-(Xmb)Gly-Thr(P)-Phe-Thr(P)-

Ser(P)-Asp(P)-pYS-Lys(P)-Tyr(P)-Leu-Asp(P)-Ser(P)-

Arg(P)-Arg(P)-Ala-Gln(P)-Asp(P)-Phe-Val-Gln(P)-

Trp(P)-Leu-Met-Asn(P)-Thr(P),

-continued (SEQ ID NO: 14)
His(P)-Ser(P)-Gln(P)-(Xmb)Gly-Thr(P)-Phe-pTS-

Asp(P)-Tyr(P)-Ser(P)-Lys(P)-Tyr(P)-Leu-Asp(P)-

Ser(P)-Arg(P)-Arg(P)-Ala-Gln(P)-Asp(P)-Phe-Val-

Gln(P)-Trp(P)-Leu-Met-Asn(P)-Thr(P), (SEQ ID NO: 15)
His(P)-Ser(P)-Gln(P)-(Xmb)Gly-Thr(P)-Phe-pTS-

Asp(P)-Tyr(P)-Ser(P)-Lys(P)-Tyr(P)-Leu-pDS-

Arg(P)-Arg(P)-Ala-Gln(P)-Asp(P)-Phe-Val-Gln(P)-

Trp(P)-Leu-Met-Asn(P)-Thr(P), (SEQ ID NO: 16)
His(P)-Ser(P)-Gln(P)-(Xmb)Gly-Thr(P)-Phe-Thr(P)-

Ser(P)-Asp(P)-pYS-Lys(P)-Tyr(P)-Leu-pDS-Arg(P)-

Arg(P)-Ala-Gln(P)-Asp(P)-Phe-Val(P)-Gln(P)-Trp(P)-

Leu-Met-Asn(P)-Thr(P), (SEQ ID NO: 17)
His(P)-Ser(P)-Gln(P)-Gly-Thr(P)-Phe-pTS-Asp(P)-

Tyr(P)-Ser(P)-Lys(P)-Tyr(P)-(Xmb)Leu-Asp(P)-

Ser(P)-Arg(P)-Arg(P)-Ala-Gln(P)-Asp(P)-Phe-Val-

Gln(P)-Trp(P)-Leu-Met-Asn(P)-Thr(P), (SEQ ID NO: 18)
His(P)-Ser(P)-Gln(P)-Gly-Thr(P)-Phe-Thr(P)-Ser(P)-

Asp(P)-pYS-Lys(P)-Tyr(P)-(Xmb)Leu-Asp(P)-Ser(P)-

Arg(P)-Arg(P)-Ala-Gln(P)-Asp(P)-Phe-Val-Gln(P)-

Trp(P)-Leu-Met-Asn(P)-Thr(P), (SEQ ID NO: 19)
His(P)-Ser(P)-Gln(P)-Gly-Thr(P)-Phe-Thr(P)-Ser(P)-

Asp(P)-Tyr(P)-Ser(P)-Lys(P)-Tyr(P)-Leu-pDS-Arg(P)-

Arg(P)-(Xmb)Ala-Gln(P)-Asp(P)-Phe-Val-Gln(P)-

Trp(P)-Leu-Met-Asn(P)-Thr(P), (SEQ ID NO: 20)
His(P)-Ser(P)-Gln(P)-(Xmb)Gly-Thr(P)-Phe-Thr(P)-

Ser(P)-Asp(P)-pYS-Lys(P)-Tyr(P)-Leu-Asp(P)-Ser(P)-

Arg(P)-Arg(P)-(Xmb)Ala-Gln(P)-Asp(P)-Phe-Val-

Gln(P)-Trp(P)-Leu-Met-Asn(P)-Thr(P),
and (SEQ ID NO: 21)
His(P)-Ser(P)-Gln(P)-Gly-Thr(P)-Phe-pTS-Asp(P)-

Tyr(P)-Ser(P)-Lys(P)-Tyr(P)-Leu-Asp(P)-Ser(P)-

Arg(P)-Arg(P)-(Xmb)Ala-Gln(P)-Asp(P)-Phe-Val-

Gln(P)-Trp(P)-Leu-Met-Asn(P)-Thr(P), wherein Xmb is selected from Tmb, Dmb, and Hmb, and P is a side-chain protecting group or is absent. The Xmb is preferably Tmb. The side-chain protecting group P is preferably selected from the group comprising tertbutyloxycarbonyl (Boc), tert-butyl (tBu), trityl (Trt) and 2,2,4,6,7-pentamethyldihydrobenzofuran-5-sulfonyl (Pbf), based on the specific amino acid.

In a preferred embodiment, the protected glucagon sequence which is an intermediate in the synthesis of glucagon is:

(SEQ ID NO: 12)
His(tBu)-Ser(tBu)-Gln(Trt)-(Xmb)Gly-Thr(tBu)-

Phe-Thr(tBu)-Ser(tBu)-Asp(tBu)-Tyr(tBu)-Ser(tBu)-

Lys(Boc)-Tyr(tBu)-Leu-pDS-Arg(Pbf)-Arg(Pbf)-

Ala-Gln(Trt)-Asp(tBu)-Phe-Val-Gln(Trt)-Trp(Boc)-

Leu-Met-Asn(Trt)-Thr(tBu).

Even more preferred, the above protected glucagon sequence is attached to a Wang resin.

The above described process may be performed by SPPS or by LPPS (Liquid Phase Peptide Synthesis) or by mixed SPPS/LPPS techniques.

Final deprotection of the protected glucagon sequence provides crude glucagon, which may optionally be purified.

In a preferred embodiment, when SPPS is used, the protected glucagon sequence is finally deprotected and cleaved from the resin, either simultaneously or in two steps, providing crude glucagon, which may optionally be purified.

Deprotection and cleavage conditions generally depend on the nature of the protecting groups and of the resin used: in a preferred embodiment, deprotection and cleavage are performed by treatment with an acid; preferably, with a mixture comprising an acid, for instance trifluoroacetic acid (TFA), or the like. Optionally, the cleavage mixture may comprise one or more scavengers. Scavengers are substances, like, for instance, anisole, thioanisole, triisopropylsilane (TIS), 1,2-ethanedithiol (EDT) and phenol, capable of minimize modification or destruction of the sensitive deprotected side chains, such as those of arginine residues, in the cleavage environment.

The crude glucagon obtained may be optionally purified by crystallization or chromatographic techniques well known in the art.

The inventors of the present invention have found that the use of the above mentioned Xmb-protected amino acids and pseudoproline dipeptide residues produces glucagon in greater yield and higher purity which, without being bound to theory, may be attributed to disruption of secondary structure formation and aggregation.

ABBREVIATIONS

SPPS Solid phase peptide synthesis
LPPS Liquid phase peptide synthesis
MBHA resin Methyl benzhydryl amide resin
Xmb Tmb or Dmb or Hmb
Tmb 2,4,6-Trimethoxybenzyl
Dmb 2,4-Dimethoxybenzyl
Hmb 2-Hydroxy-4-methoxybenzyl
Fmoc 9-fluorenylmethyloxycarbonyl
Boc t-Butyloxycarbonyl
Trt Trityl
tBu Tert-butyl
Pbf 2,2,4,6,7-pentamethyldihydrobenzofuran-5-sulfonyl
HPLC High performance liquid chromatography
h/min hour/minutes
DIEA Diisopropylethylamine
DBU 1,8-Diazabicyclo[5.4.0]undec-7-ene
DMAP 4-DimethylaminopyridineTFA Trifluoroacetic acid
Ac₂O Acetic anhydride DMF N,N-Dimethylformamide
DCM Dichloromethane
ACN Acetonitrile
MeOH Methanol
TIS Triisopropylsilane
EDT 1,2-ethanedithiol
DIC Diisopropylcarbodiimide
DCC Dicyclohexylcarbodiimide
EDC Ethyl-dimethylaminopropyl carbodiimide
HOBt 1-Hydroxybenzotriazole
HOAt 1-Hydroxy-7-azabenzotriazole
TBTU N,N,N',N'-Tetramethyl-O-(benzotriazol-1-yl)uronium tetrafluoroborate
HBTU 3-[Bis(dimethylamino)methyliumyl]-3H-benzotriazol-1-oxide hexafluorophosphate
HATU 2-(7-Aza-1H-benzotriazole-1-yl)-1,1,3,3-tetramethyluronium hexafluorophosphate
PyBOP (Benzotriazol-1-yloxy)-tripyrrolidinophosphoniumhexafluorophosphate
Oxyma/OxymaPure Ethyl 2-cyano-2-hydroxyimino-acetate

EXPERIMENTAL PART

Detailed experimental conditions suitable for the preparation of glucagon according to the present invention are provided by the following examples, which are intended to be illustrative and not limiting of all possible embodiments of the invention.

Unless otherwise noted, all materials, solvents and reagents were obtained from commercial suppliers, of the best grade, and used without further purification.

Assays (%) are calculated by HPLC, comparing the peak area of the sample with the peak area of the standard. The molar yields (%) are calculated considering the final moles obtained (based on Assay) divided by the initial moles.

EXAMPLE 1

Preparation of Glucagon

Loading of Resin

Synthesis of glucagon was carried out by SPPS on Wang resin (3 grams). After swelling the resin with DMF (10 mL), Fmoc-Thr(tBu)-OH (4 eq with respect to the loading of the resin) was pre-activated with DIC and DMAP (2 and 0.1 eq, respectively) for 5 min in DMF (18 mL), then added to the resin and coupled for 60 min. The resin was then washed with DMF (3×6 mL) and the residual free hydroxyl groups were capped with Ac$_2$O 0.5 M in DMF (6 mL for 15 min) and washed with DMF (3×6 mL). Fmoc group was removed by treatment with 20% piperidine in DMF (2×6 mL, 10 min for cycle) and washed with DMF (4×6 mL, 2×5 min and 2×10 min). The loading of the resin after the insertion of the first amino acid was evaluated by UV measurement of the deprotection solution at 301 nm, providing a loading of 0.7 mmol/g.

The resin thus obtained was split in three portions (1 gram of starting resin each): one was used for the SPPS synthesis of glucagon employing only standard Fmoc-protected aminoacids (Lot 1A), the second one employing the pseudoproline dipeptide residue Fmoc-Asp(OtBu)-Ser[psi(Me,Me)pro]-OH (positions 15-16, Lot 1B), and the third one employing both the pseudoproline dipeptide residue Fmoc-Asp(OtBu)-Ser[psi(Me,Me)pro]-OH and the N,N-bisprotected glycine residue Fmoc(Tmb)-Gly-OH (Lot 1C).

Lot 1A (Reference)

Preparation was carried out by employing the following amino acids, ordered from the first to the last attached to H-Thr-Wang resin obtained as described above:
Fmoc-Asn(Trt)-OH, Fmoc-Met-OH, Fmoc-Leu-OH, Fmoc-Trp(Boc)-OH, Fmoc-Gln(Trt)-OH, Fmoc-Val-OH, Fmoc-Phe-OH, Fmoc-Asp(tBu)-OH, Fmoc-Gln(Trt)-OH, Fmoc-Ala-OH, Fmoc-Arg(Pbf)-OH, Fmoc-Arg(Pbf)-OH, Fmoc-Ser(tBu)-OH, Fmoc-Asp(tBu)-OH, Fmoc-Leu-OH, Fmoc-Tyr(tBu)-OH, Fmoc-Lys(Boc)-OH, Fmoc-Ser(tBu)-OH, Fmoc-Tyr(tBu)-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Gln(Trt)-OH, Fmoc-Ser(tBu)-OH, Boc-His(Trt)-OH.

In each step, the Fmoc-protected amino acid (4 eq with respect to resin loading, i.e., 2.8 mmol) was pre-activated with DIC (4 eq) and OxymaPure (4 eq) for 3 min in DMF (6 mL), then added to the resin and coupled for 60 min. After each coupling, the unreacted amino groups were capped using Ac$_2$O 0.5 M in DMF. Fmoc groups were removed by treatment with 20% piperidine in DMF (2×6 mL, 10 min per cycle) and subsequent washing of the resin with DMF (4×6 mL, 2×5 min and 2×10 min), to allow the insertion of the next amino acid residue. After completion of the peptide sequence, the peptidyl resin was washed with DMF (3×6 mL), DCM (3×6 mL) and dried up to constant weight. Dry peptidyl resin was suspended in 20 mL of a TFA/TIS/H$_2$O/EDT/Methionine/NH$_4$I (92.5:2:2:2:1:0.5 v/v/v/v/w/w) mixture, pre-cooled to 0-5° C. and stirred for 4 h at room temperature. The resin was filtered off and cold diisopropylether (80 mL) was added to the solution. The obtained pale yellow suspension was stirred at 0-5° C. The solid was filtered, washed further 3 times with 20 mL of diisopropylether and dried in vacuo to get 2.4 g of crude glucagon (0.10 mmol, assay 15%) with an HPLC purity of 37%. Molar Yield: 15%.

Lot 1B (Reference)

Preparation was carried out by employing the following amino acids and peptides, ordered from the first to the last attached to H-Thr-Wang resin obtained as described above:
Fmoc-Asn(Trt)-OH, Fmoc-Met-OH, Fmoc-Leu-OH, Fmoc-Trp(Boc)-OH, Fmoc-Gln(Trt)-OH, Fmoc-Val-OH, Fmoc-Phe-OH, Fmoc-Asp(tBu)-OH, Fmoc-Gln(Trt)-OH, Fmoc-Ala-OH, Fmoc-Arg(Pbf)-OH, Fmoc-Arg(Pbf)-OH, Fmoc-Asp(OtBu)-Ser[psi(Me,Me)pro]-OH, Fmoc-Leu-OH, Fmoc-Tyr(tBu)-OH, Fmoc-Lys(Boc)-OH, Fmoc-Ser(tBu)-OH, Fmoc-Tyr(tBu)-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Gln(Trt)-OH, Fmoc-Ser(tBu)-OH, Boc-His(Trt)-OH.

In each step, the Fmoc-protected amino acid (4 eq with respect to resin loading, i.e., 2.8 mmol) was pre-activated with DIC (4 eq) and OxymaPure (4 eq) for 3 min in DMF (6 mL), then added to the resin and coupled for 60 min. Pseudoproline residue Fmoc-Asp(OtBu)-Ser[psi(Me,Me)pro]-OH (3 eq) was coupled after pre-activation with DIC and OxymaPure (3 eq) for 3 min in DMF (6 mL), then added to the resin and coupled for 90 min. After each coupling, the unreacted amino groups were capped using Ac$_2$O 0.5 M in DMF. Fmoc groups were removed by treatment with 20% piperidine in DMF (2×6 mL, 10 min per cycle) and subsequent washing of the resin with DMF (4×6 mL, 2×5 min and 2×10 min), to allow the insertion of the next residue. After completion of the peptide sequence, the peptidyl resin was washed with DMF (3×6 mL), DCM (3×6 mL) and dried up to constant weight. Dry peptidyl resin was suspended in 20 mL of a TFA/TIS/$H_2O$/EDT/L-Methionine/$NH_4I$ (92.5:2:2:2:1:0.5 v/v/v/v/w/w) mixture, pre-cooled to 0-5° C. and stirred for 4 h at room temperature. The resin was filtered off and cold diisopropylether (80 ml) was added to the solution. The obtained pale yellow suspension was stirred at 0-5° C. The solid was filtered, washed further 3 times with 20 mL of diisopropylether and dried in vacuo to get 1.7 g of crude glucagon (0.02 mmol, assay 4%) with an HPLC purity of 8%. Molar Yield: 3%.

Lot 1C

Preparation was carried out by employing the following amino acids and peptides, ordered from the first to the last attached to H-Thr-Wang resin obtained as described above:

Fmoc-Asn(Trt)-OH, Fmoc-Met-OH, Fmoc-Leu-OH, Fmoc-Trp(Boc)-OH, Fmoc-Gln(Trt)-OH, Fmoc-Val-OH, Fmoc-Phe-OH, Fmoc-Asp(tBu)-OH, Fmoc-Gln(Trt)-OH, Fmoc-Ala-OH, Fmoc-Arg(Pbf)-OH, Fmoc-Arg(Pbf)-OH, Fmoc-Asp(OtBu)-Ser[psi(Me,Me)pro]-OH, Fmoc-Leu-OH, Fmoc-Tyr(tBu)-OH, Fmoc-Lys(Boc)-OH, Fmoc-Ser(tBu)-OH, Fmoc-Tyr(tBu)-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc(Tmb)-Gly-OH, Fmoc-Gln(Trt)-OH, Fmoc-Ser(tBu)-OH, Boc-His(Trt)-OH.

In each step, the Fmoc-protected amino acid (4 eq with respect to resin loading, i.e., 2.8 mmol) was pre-activated with DIC (4 eq) and OxymaPure (4 eq) for 3 min in DMF (6 mL), then added to the resin and coupled for 60 min. Pseudoproline residue Fmoc-Asp(OtBu)-Ser[psi(Me,Me)pro]-OH (3 eq) and N,N-bis-protected glycine Fmoc(Tmb)-Gly-OH (3 eq) were coupled after pre-activation with DIC and OxymaPure (3 eq) for 3 min in DMF (6 mL), then added to the resin and coupled for 90 min. After each coupling, the unreacted amino groups were capped using $Ac_2O$ 0.5 M in DMF. Fmoc groups were removed by treatment with 20% piperidine in DMF (2×6 mL, 10 min per cycle) and washed with DMF (4×6 mL, 2×5 min and 2×10 min), to allow the insertion of the next residue. After completion of the peptide sequence, the peptidyl resin was washed with DMF (3×6 mL), DCM (3×6 mL) and dried up to constant weight. Dry peptidyl resin was suspended in 20 mL of a TFA/TIS/$H_2O$/EDT/L-Methionine/$NH_4I$ (92.5:2:2:2:1:0.5 v/v/v/v/w/w) mixture, pre-cooled to 0-5° C. and stirred for 4 h at room temperature. The resin was filtered off and cold diisopropylether (80 ml) was added to the solution. The obtained pale yellow suspension was stirred at 0-5° C. The solid was filtered, washed further 3 times with 20 mL of diisopropylether and dried in vacuo to get 2.6 g of crude glucagon (0.38 mmol, assay 50%) with an HPLC purity of 70%. Molar Yield: 55%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for the preparation of glucagon of formula I

```
                                                                    (I)
            1           5               10
        His-Ser-Gln-Gly-Thr-Phe-Thr-Ser-Asp-Tyr- 15              20
        Ser-Lys-Tyr-Leu-Asp-Ser-Arg-Arg-Ala-Gln- 25          29
        Asp-Phe-Val-Gln-Trp-Leu-Met-Asn-Thr,
``` the process comprising stepwise coupling of amino acids or peptides to resin to generate an intermediate C-terminal peptide of glucagon, wherein at least one step comprises coupling with an Xmb-protected Gly and at least one step comprises coupling with a pseudoproline dipeptide, wherein Xmb is 2,4,6-trimethoxybenzyl (Tmb), 2,4-dimethoxybenzyl (Dmb), or 2-hydroxy-4-methoxybenzyl group (Hmb), and the pseudoproline dipeptide is selected from:

Fmoc-Asp(P)-Ser[psi($R_1$, $R_1$)pro]-OH (Fmoc-pDS),
Fmoc-Tyr(P)-Ser[psi($R_1$, $R_1$)pro]-OH (Fmoc-pYS), and
Fmoc-Thr(P)-Ser[psi($R_1$, $R_1$)pro]-OH (Fmoc-pTS), wherein P is a protecting group or is absent, and $R_1$ is hydrogen or methyl, and wherein one of the following C-terminal peptides is used as an intermediate:

```
                                            (SEQ ID NO: 2)
(Xmb)Gly-Thr(P)-Phe-Thr(P)-Ser(P)-Asp(P)-Tyr(P)-

Ser(P)-Lys(P)-Tyr(P)-Leu-pDS-Arg(P)-Arg(P)-Ala-

Gln(P)-Asp(P)-Phe-Val-Gln(P)-Trp(P)-Leu-Met-

Asn(P)-Thr(P), (SEQ ID NO: 5)
(Xmb)Gly-Thr(P)-Phe-pTS-Asp(P)-Tyr(P)-Ser(P)-

Lys(P)-Tyr(P)-Leu-pDS-Arg(P)-Arg(P)-Ala-Gln(P)-

Asp(P)-Phe-Val-Gln(P)-Trp(P)-Leu-Met-Asn(P)-

Thr(P), or (SEQ ID NO: 6)
(Xmb)Gly-Thr(P)-Phe-Thr(P)-Ser(P)-Asp(P)-pYS-

Lys(P)-Tyr(P)-Leu-pDS-Arg(P)-Arg(P)-Ala-Gln(P)-

Asp(P)-Phe-Val(P)-Gln(P)-Trp(P)-Leu-Met-Asn(P)-

Thr(P),
``` and converting the C-terminal peptide into glucagon of formula I.

2. The process according to claim 1, wherein the Xmb is Tmb.

3. The process according to claim 1, wherein the pseudoproline dipeptide is selected from:

Fmoc-Asp(OtBu)-Ser[psi(Me, Me)pro]-OH
Fmoc-Tyr(tBu)-Ser[psi(Me, Me)pro]-OH
and
Fmoc-Thr(tBu)-Ser[psi(Me, Me)pro]-OH.

4. The process according to claim 1, wherein the intermediate C-terminal peptide is:

```
                                            (SEQ ID NO: 2)
(Tmb)Gly-Thr(tBu)-Phe-Thr(tBu)-Ser(tBu)-

Asp(tBu)-Tyr(tBu)-Ser(tBu)-Lys(Boc)-Tyr(tBu)-

Leu-pDS-Arg(Pbf)-Arg(Pbf)-Ala-Gln(Trt)-

Asp(tBu)-Phe-Val-Gln(Trt)-Trp(Boc)-Leu-Met-

Asn(Trt)-Thr(tBu),
``` wherein pDS is Asp(OtBu)-Ser[psi(Me, Me)pro].

5. The process according to claim 1, wherein the intermediate C-terminal peptide is attached to a solid support at the C-terminal end.

6. The process according to claim 5, wherein the solid support is a Wang resin.

7. The process according to claim 1, wherein at least one coupling reagent is diisopropylcarbodiimide, dicyclohexylcarbodiimide, (Benzotriazol-1-yloxy)tripyrrolidinophosphonium hexafluorophosphate, 2-(7-Aza-1H-benzotriazole-1-yl)-1,1,3,3-tetramethyluronium hexafluorophosphate, 2-(1H-benzotriazole-1-yl)-1,1,3,3-tetramethyluronium hexafluorophosphate, or ethyl-dimethylaminopropyl carbodiimide.

8. The process according to claim 7, wherein the coupling reagent is diisopropylcarbodiimide, which is used in the presence of ethyl 2-cyano-2-hydroxyimino-acetate.

9. The process according to claim 1, wherein the side-chain protecting group P is tertbutyloxycarbonyl, tert-butyl, trityl, or 2,2,4,6,7-pentamethyldihydrobenzofuran-5-sulfonyl.

10. The process according to claim 1, wherein the side-chain protecting group P is tertbutyloxycarbonyl, tert-butyl, trityl, or 2,2,4,6,7-pentamethyldihydrobenzofuran-5-sulfonyl.

* * * * *